United States Patent [19]
Wong

[11] Patent Number: 4,500,507
[45] Date of Patent: Feb. 19, 1985

[54] DIAGNOSTIC COMPOSITION FOR RADIOLOGIC IMAGING OF NEOPLASMS IN THE BODY AND METHOD OF PREPARATION

[76] Inventor: Dennis W. Wong, 2853 Sunnyglen Rd., Torrance, Calif. 90505

[21] Appl. No.: 316,957

[22] Filed: Oct. 30, 1981

[51] Int. Cl.³ .................... A61K 29/00; A61K 49/00
[52] U.S. Cl. ........................ 424/1.1; 424/9; 260/245.91
[58] Field of Search ................... 424/1, 1.5, 9

[56] References Cited

PUBLICATIONS

Sanderson et al., Cancer, vol. 30, (1972): 1368–1372.
Bases et al., Cancer, vol. 11, (1958): 259–263.
Lipson et al., J. Natl. Cancer Inst., vol. 26, (1961): 1–11.

*Primary Examiner*—Christine M. Nucker

[57] ABSTRACT

A novel chemical method of labeling porphyrin compounds, specifically hematoporphyrin derivative (HPD), with the radionuclide Technetium-99m producing a radioactive tracer material suitable for biomedical applications. HPD labeled with $^{99m}$Tc is biologically active in vivo and is preferentially taken up by neoplastic tissues. This provides a simple and specific means of visualizing tumors in man or animal by scintigraphic imaging techniques.

25 Claims, No Drawings

DIAGNOSTIC COMPOSITION FOR RADIOLOGIC IMAGING OF NEOPLASMS IN THE BODY AND METHOD OF PREPARATION

BACKGROUND OF THE INVENTION

The lack of improvement in cure rate of many common neoplasms is amply documented and often ascribed to failure of early detection. Present clinical means for detecting neoplastic tissue remain in many instances a gross anatomic procedure relying upon various physical findings or radiographic imaging procedures to select a site for histologic sampling. Scintillation imaging techniques with radiopharmaceuticals such as $^{67}$Ga-Gallium citrate, $^{111}$In-Bleomycin and $^{131}$I-Diiodofluorescein have limited success. These radiolabeled compounds lack specificity and sensitivity, that is, they are not preferentially taken up by neoplasms or tumors. Both $^{67}$Ga-Gallium citrate and $^{111}$In-Bleomycin are accumulated in inflammatory or infectious lesions. Currently, all available diagnostic techniques have many drawbacks and limitations in addition to lack of sensitivity and specificity. These include the use of traumatic invasive procedures and potential for serious complications.

Attempts to "mark" or "tag" cancer cells in order to differentiate them from normal tissues are not new. Various fluorescent compounds such as porphyrins, tetracycline derivatives, acridine orange and toluidine blue or radioactive isotopes have been extensively investigated. With the exception of porphyrin compounds, none of these substances used by earlier investigators are capable of routinely identifying and delineating malignant lesions.

To be effective, an ideal marker substances should: (1) be safe and non-toxic in humans; (2) selectively accumulate only in neoplastic tissue and not be taken up by normal or inflammatory tissues; (3) be simple to use and involve non-invasive procedures; (4) be capable of being documented by photographs, radiographs or other recording devices. The ideal marker or tracer continues to remain elusive, but derivatives of porphyrin appear to satisfy several of these requirements.

Porphyrins are complex tetrapyrrole compounds normally found in plants and in animals. They perform many vital biological functions by combining with metallic ions such as iron, magnesium, manganese, zinc, etc ... to form metalloporphyrins. Metalloporphyrins such as hemoglobin, myosin, vitamin B-12, cytochrome, catalase, peroxidase and chlorophyll are essential for the normal metabolism of plants and animals. Many of these porphyrins and metalloporphyrins exhibit strong fluorescence when exposed to an appropriate exciting light source.

Hematoporphyrin, an artificial porphyrin compound, is prepared by treating hemoglobin with concentrated sulfuric acid ($H_2SO_4$). It is a crude mixture of several porphyrins. The exact chemical composition of hematoporphyrin has not been identified.

The preferential affinity of porphyrins and hematoporphyrin for neoplastic tissue has been known for more than four decades. When injected into tumor-bearing animals, a brilliant red-orange fluorescence is produced by ultra violet(UV) light activation of the porphyrins or hematoporphyrin accumulated in the tumors. Hematoporphyrin appears to be a better tumor localizer than any porphyrin compounds.

Hematoporphyrin derivative (HPD), a recrystallized form of hematoporphyrin developed by Lipson and associates (Lipson, et al., *J. Nat. Cancer Inst.* 26: 1-11,1961) possesses higher tumor selectivity than earlier porphyrin compounds. It is currently the most actively investigated version of porphyrins for tumor identification and treatment. Clinical applications of HPD in tumor detection have been reported in the literature (Sanderson, et al., Cancer. 30: 1368, 1972 and Kinsey, et al., Mayo Clin. Proc. 53: 594, 1978).

Despite the initial optimism over possible diagnostic application of HPD, the usefulness of this compound is limited. This is primarily due to the fact that HPD-fluorescence method involves invasive procedures. The fluorescence emitted by HPD must be activated in situ by a strong ultra violet light source which requires highly sophisticated endoscopic optical equipments. Visual observation of the tissue fluorescence at best is subjective & varies widely from different investigators. Quenching of the fluorescence by normal tissue, body fluids and blood is a major obstacle in achieving significant reliability and reproducibility of this technique. Endoscopic procedures often produce tissue damages which lead to hemmorhage and subsequent masking of the tumor. Another major problem is the inability to document photographically the fluorescence observed endoscopically. Complete reliance has to be placed on the visual interpretation and judgement of the endoscopist.

The use of radiolabeled HPD will eliminate most of the major problems encountered by the fluorescence-endoscopic method. Nuclear medicine procedures employing radiopharmaceuticals are simple and non-invasive. Following parenteral administration of the radiolabeled HPD, the radioactivity which concentrated in the neoplastic lesions can be easily detected and documented by scintigraphic imaging techniques.

Various porphyrin compounds had been labeled with radionuclides such as $^{64}$Cu and $^{57}$Co. Protoporphyrin and hematoporphyrin labeled with $^{64}$Cu were shown to concentrated in mouse tumors but failed to achieve significant tumor uptake in human beings (Base, R. et al, Cancer 11: 259, 1958). Similar results were obtained with $^{57}$Co-labeled hemtoporphyrin (Anghileri, LJ, et al: Nucl. Med. 15: 183, 1976). Earlier failures to localize human neoplasms with radiolabeled porphyrin compounds were attributed to: (1) poor labeling methodology; (2) the radionuclides used in the labeling process were incompatible with conventional scintigraphic imaging equipment; (3) in vivo instability of the labeled porphyrins; (4) alteration in biochemical properties after labeling process.

Technetium-99m ($^{99m}$Tc) based radiopharmaceuticals have been widely used in the past 15 years. They are by far the safest and the most useful scintigraphic imaging agents developed for Nuclear Medicine procedures. The radionuclide $^{99m}$Tc has many advantages. It is a pure gamma emitter with a relatively short physical half life of six hours. The gamma photon of 140 KeV energy is compatible with existing conventional scintillation imaging equipments. $^{99m}$Tc-radiopharmaceuticals can be administered to patients in a much larger dose than many other radiolabeled compounds but produces a minimal radiation health hazard.

Currently, all $^{99m}$Tc-based radiopharmaceuticals are produced based on the stannous(Sn)-acid reduction method (Eckelman, W. C., U.S. Pat. No. 3,725,295, 4/73). According to the labeling methodology, $^{99m}$Tc(+7) in the stable form of sodium pertechnetate ($Na^{99m}TcO_4$) is first reduced to a chemically active (+4) or (+5) valence state with a reducing agent such as tin chloride(stannous chloride, $SnCl_2$) which is dissolved in weak hydrochloric acid (HCl). Reduction of $^{99m}Tc$-pertechnetate occurs at acidic condition with a pH of less than 2. An aqueous solution of the compound to be labeled is added to the reduced $^{99m}Tc/Sn(II)$ acidic mixture with the subsequent covalent binding of the radionuclide to the compound. The final mixture is then adjusted to pH 4–6 with a suitable buffer. The exact labeling mechanism is not known. With the exception of the chelates, other compounds or biological substances such as human serum albumin and red blood cells labeled by the Sn(II)-acid reduction method are completely denatured with significant loss of biochemical and physiological properties.

An alkaline Sn(II)-reduction method of labeling protein substances with $^{99m}Tc$ has been reported (Abramovici, et al, U.S. Pat. No. 4,057,617, 11/77). According to this invention, the proteins antibody and fibrinogen have claimed to be labeled with $^{99m}Tc$ at pH 11.6 condition. Technetium-99m pertechnetate is first reduced at pH 11.6 by adding an alkaline solution containing stannous chloride, acetic acid and sodium hydroxide(NaOH). The protein solution is then brought in contact with the reduced $^{99m}Tc$ forming a radiolabeled protein. The mixture is readjusted to pH 7.4 with a suitable buffer. The problems encountered by labeling protein substances at alkaline pH condition are similar to the acid reduction method, namely; protein denaturation, formation of insoluble radioactive tin colloids, protein degradation products, free or unbound $^{99m}Tc$ and very low yield. The labeling process of Abramovici is ineffective for producing useful radioactive tracer materials.

A simple chemical method of labeling protein substances with $^{99m}Tc$ under physiological condition has been developed by the present inventor (Wong, D. W., U.S. Pat. No. 4,293,537, 10/81 and Wong, D. W., et al, Int. J. Appl. Rad. Isotopes 29: 251, 1978). The basic labeling process involves the production of a chemically active $^{99m}Tc$-(Sn)citrate complex species at pH 7.4 condition following initial reduction of $^{99m}Tc$-pertechnetate. An aqueous protein solution is brought in contact with the radioactive complexing species forming a stable radiolabeled product. Unlike existing labeling processes, the actual labeling of the protein ligand with $^{99m}Tc$ occurs at physiological condition. Experimental data have confirmed that plasma proteins such as fibrinogen, antibodies, protein enzymes and hormones labeled with $^{99m}Tc$ by the physiologic chemical process are not denatured but retain their natural biochemical and immunological properties (Wong, D. W. et al, J. Nucl. Med. 20: 967, 1979 1979 and Wong, D. W. et al, J. Nucl. Med. 22: 229, 1981). Further investigation of this labeling process indicates that the $^{99m}Tc$-(Sn)citrate complex species can tag many other compounds such as chelates and porphyrins in addition to protein substances.

Technetium-99m labeled hematoporphyrin derivative ($^{99m}Tc$-HPD) offers many advantages over the fluorescence-endoscopic technique. Among these are: (1) the radionuclide $^{99m}Tc$ is firmly bound to the HPD ligand; (2) $^{99m}Tc$-HPD is biologically active and remains stable in vivo; (3) it exhibits strong fluorescence when activated by UV light source; (4) Unlike other radiolabeled metalloporphyrins, $^{99m}Tc$-HPD is preferentially accumulated by neoplastic tissue which can be documented by scintigraphic imaging techniques; (5) it can be administered to patients by parenteral routes; (6) it is safe and non-toxic; (7) the labeling process is so simple that a non-radioactive labeling reagent kit with long shelve life can be prepared in advance prior to actual use.

SUMMARY OF THE INVENTION

A novel diagnostic composition comprises a fluorescent compound hematoporphyrin derivative(HPD), a stannous reducing agent and an alkaline sodium citrate solution aseptically prepared in sealed sterile non-pyrogenic containers and packaged as an instant non-radioactive labeling reagent kit. The said labeling reagent kit is to be used in conjunction with a source of $^{99m}Tc$-pertechnetate forming an efficiently labeled radioactive tracer material suitable for use as a tumor scintigraphic imaging agent. In the process of preparing $^{99m}Tc$-HPD injection, a solution of $^{99m}Tc$-pertechnetate in normal saline is first added to the lyophilized stannous chloride/0.05N hydrochloric acid powder which when dissolved causes chemical reduction of the radionuclide. The reduced $^{99m}Tc$ is treated with a pH 12.4 solution of sodium citrate/sodium hydroxide forming a chemically active $^{99m}Tc$-(Sn)citrate complex species at pH 7.4 condition. An aqueous solution of HPD is brought in contact with the $^{99m}Tc$-(Sn)citrate complexing species forming a stable $^{99m}Tc$-labeled HPD suitable for parenteral administration. Following intravenous injection, $^{99m}Tc$-HPD is rapidly taken up by neoplastic tissues with increased radioactivity accumulating at these sites. This provides a simple and rapid means of localizing and detecting the presence of neoplasms in man and in animal by scintillation imaging procedures.

DETAILED DESCRIPTION OF THE INVENTION

This invention relates to the development of a novel radiopharmaceutical useful for localization and detection of neoplasms. Specifically, it relates to a chemical method of labeling hematoporphyrin derivative (HPD) with the radionuclide of Technetium $^{99m}Tc$ producing a radiolabeled substance suitable for biological and medical applications. The invention further relates to a prepackaged non-radioactive labeling reagent kit based on the said labeling process and a simple method of using said labeling reagent kit for producing $^{99m}Tc$-HPD injection with generally available $^{99m}Tc$-pertechnetate normal saline solution.

Basically, the labeling process requires the following sequential steps of: (1) initial reduction of $^{99m}Tc$-pertechnetate by a stannous reducing agent; (2) the formation of a chemically active $^{99m}Tc$-(Sn)citrate complexing species by the reaction of reduced $^{99m}Tc$ in (+4) or (+5) valence state with a solution of sodium citrate; (3) raising the pH of the acidic radioactive mixture to 7.4 with sodium hydroxide (NaOH) solution; (4) covalent binding of the reduced $^{99m}Tc$ to the HPD molecules by the addition of an aqueous solution of HPD. Thus, in the present invention, the actual labeling of HPD with $^{99m}Tc$ occurs at pH 7.4. Data from radiochemical analyses have confirmed that $^{99m}Tc$ is firmly bound to the HPD molecule. The labeling yield is greater than 97% with less than 3% free or unbound $^{99m}Tc$. The radiolabeled product is ready for immediate use without any additional purification process. To facilitate the labeling process, the chemical reaction in steps 2 and 3 can be combined into a single step using an alkaline pH 12.4 solution of sodium citrate and NaOH.

Based on the chemical labeling process described above, an instant non-radioactive labeling reagent kit can be prepared in advance with individual components packaged separately in sealed, sterile non-pyrogenic containers. Such a labeling reagent kit is comprised of three basic components: (1) a sterile solution of stannous chloride dissolved in 0.05-0.1N hydrochloric acid (HCl); (2) a 2% sodium citrate solution made alkaline to pH 12.4 with 1N NaOH and (3) an aqueous solution of HPD in a concentration of 5-10 mg/ml dissolved in pH 7.4 normal saline (0.9% NaCl) solution. All three reagents are aseptically prepared and sterilized by conventional means. The labeling reagent kit is to be used in conjunction with a source of $^{99m}$Tc-pertechnetate such as that generally eluted from a Technetium generator.

Any stannous salts such as stannous chloride ($SnCl_2$), stannous fluoride (SnF), or stannous tartrate can be used for the chemical reduction of $^{99m}$Tc-pertechnetate. In the present embodiment, stannous chloride is preferred. The stannous reducing agent is prepared by dissolving the desired amount of $SnCl_2$ in 0.05N HCl solution. One-half to 1 ml of the reducing agent containing 0.1-5 mg of $SnCl_2$ is packaged in a sealed nitrogen-purged ampoule or serum vial. Preferably, the stannous reducing agent is prepared and packaged in the form of a freeze-dried solid which aids in shipping and storage. The lyophilized solid mixture of stannous chloride and HCl can be reconstituted with $^{99m}$Tc-pertechnetate normal saline solution without loss of its reducing activity.

The source of Technetium should be water soluble, with preferred sources being alkali and alkaline earth metal pertechnetate. Technetium-99m is preferably obtained in the form of fresh sodium pertechnetate ($Na^{99m}TcO_4$) from a sterile Technetium generator. Any other sources of pharmacologically acceptable $^{99m}$Tc can be used, and a number of Technetium generators are available.

Alkaline sodium citrate solution is prepared by dissolving 2% W/V of trisodium citrate crystals in distilled water and adjusted to pH 12.4 with 1N NaOH. One to 2 ml of this reagent is packaged in a sealed, sterile apyrogenic container. While it is preferred that an alkaline sodium citrate/NaOH solution be used to produce the $^{99m}$Tc-(Sn)citrate complex species and to raise the pH to 7.4 condition prior to the addition of HPD solution, the same result can be achieved using two separate reagents, that is, a 2% sodium citrate solution and a 0.1-1N NaOH solution. However, the sodium citrate solution must be added first to react with the reduced $^{99m}$Tc prior to pH adjustment with NaOH. The amount of NaOH solution needed can be determined by a simple routine experiment by those skilled in the art. The alkaline sodium citrate/NaOH solution is stable when kept refrigerated at 2°-8° C. To maintain a proper pH environment, it should be packaged in the form of a lyophilized solid. The lyophilized powder is to be reconstituted with 1-2 ml distilled water at time of use.

Hematoporphyrin derivative (HPD) is prepared by the method of Lipson (Lipson, R. L., et al: *J. Nat. Cancer Inst.* 26: 1, 1961). Hematoporphyrin hydrochloride is dissolved in a mixture of 19 parts glacial acetic acid and 1 part concentrated sulfuric acid ($H_2SO_4$) and allowed to stand at room temperature for 5-10 minutes. HPD is precipitated out from solution by the addition of 20 volumes of 3% sodium acetate solution. The precipitate is removed by filtration, thoroughly washed with distilled water and allowed to dry in the dark at room temperature overnight. The yield is approximately 80% HPD. HPD precipitate is dissolved in normal saline (0.9% NaCl) and alkalized with 1N NaOH to a pH 11.5. After complete dissolution, the HPD solution is quickly brought down to pH 7.4 with 1N HCl. It is essential that the pH of the HPD solution be maintained above pH 7.4 to avoid reprecipitation. HPD is unstable in acidic medium. At a pH of below 7, it will be precipitated out from solution. The neutralized HPD solution is sterilized by ultrafiltration technique and packaged in dark amber-colored ampoule or serum vial in a concentration of 5-10 mg/ml. Lyophilization of this reagent is unnecessary since HPD solution is stable indefinitely at room temperature or at refrigeration temperature of 2°-8° C. Any pharmacologically acceptable buffers having a pH above 7.4 such as phosphate, citrate or bicarbonate buffer systems can be used to stabilize the HPD solution.

The amount of HPD that can be labeled with $^{99m}$Tc varies from 0.1-100 mg. In the present invention, 0.5-1 ml solution containing 5-10 mg of HPD is sufficient to bind up to 200 mCi of $^{99m}$Tc.

In use, the labeling reagent kit of the present invention is to be mixed with a source of $^{99m}$Tc-pertechnetate in normal saline to form an efficiently labeled $^{99m}$Tc-HPD suitable for scintigraphic imaging of neoplasms. $^{99m}$Tc-HPD injection is prepared by a simple three-steps procedure. In the first step, using aseptic technique, 2-3 ml of $^{99m}$Tc-pertechnetate in normal saline providing 60-200 mCi of radioactivity is drawn into a syringe and is injected into the reaction vial containing the lyophilized stannous reducing agent. Reduction of $^{99m}$Tc to a chemically active state occurs when the lyophilized stannous powder is dissolved by $^{99m}$Tc-pertechnetate solution. The content of the reaction vial is shaken for 1-10 minutes to ensure complete reduction of the radionuclide. In the second step, a sufficient amount of reconstituted pH 12.4 sodium citrate/NaOH solution is added to the reduced $^{99m}$Tc solution to form the $^{99m}$Tc-(Sn)citrate complex species and to produce a pH 7.4 condition prior to the addition of HPD solution. The amount of citrate solution required generally ranges from 0.5-1 ml. In the third step, 1 ml of the HPD solution having 5-10 mg of HPD is aseptically injected into the reaction vial containing the neutralized radioactive mixture resulting from step (2) and is allowed to incubate at room temperature for 10-30 minutes. After incubation period, the final labeled product is ready for use without any additional purification steps.

The present invention is not limited to the preparation of $^{99m}$Tc-HPD. Other radionuclides of Technetium, such as $^{95m}$Tc and $^{99}$Tc are equally applicable in the labeling process. Depending on clinical applications, compounds labeled with $^{95m}$Tc or $^{99m}$Tc are ideal scintigraphic imaging agents; whereas, $^{99}$Tc-labeled substances may find wide range of applications in in vitro assays. The longer physical half life of $^{95m}$Tc (61 days) provides an added advantage, that is, compounds such as HPD labeled with $^{95m}$Tc are extremely useful for imaging procedures requiring observation periods of days rather than hours. The same non-radioactive labeling reagent kit can be used for preparing $^{99}$Tc or $^{95m}$Tc-HPD according to the labeling procedure described above. It is essential that $^{99}$Tc or $^{95m}$Tc-pertechnetate in normal saline be used in conjunction with said labeling-reagent kit.

The present chemical labeling process can also "tag" or "label" other porphyrins and related compounds with the radionuclides of Technetium. A variety of these substances are commercially available in relatively pure form. These include coproporphyrins, protoporphyrins, uroporphyrins and their respective analogs. It is essential that these porphyrin compounds are dissolved in aqueous media such as normal saline or suitable buffers having a pH of above 7.4.

The efficacy of $^{99m}$Tc-HPD to localize and to detect tumors was investigated with outbred CFW strain Swiss-Webster white mice. These animals had a high incidence of spontaneous mammary adenocarcinomas which matastasize to lungs, liver and other viscera. Animals with large tumors were selected for scintigraphic imaging and tissue distribution studies. Normal healthy mice of the same species were used as controls. Following intraperitoneal(I.P.) injection of 5 mCi $^{99m}$Tc-HPD, whole body anterior scintigraphic images or scans were obtained at various time intervals, e.g. from 0.5 to 24 hours, with an Anger scintillation camera. Increased radioactivity at the sites of the lesions indicated the presence of neoplasms. After imaging, the animals were sacrificed. Tissue samples of the tumors, various organs and blood were collected, weighed and assayed for radioactivity. Percent uptake of $^{99m}$Tc-HPD in the tumor and other organs was determined by assaying the radioactivity of the samples in a welltype gamma scintillation counter against a standard containing 1:1000 of the injected dose. Microsopic tissue slides from tissue samples were obtained for histologic identification of the tumors.

Imaging results confirmed that $^{99m}$Tc-labeled HPD localized in malignant and benign tumors. All viable tumors were visualized in the 3 hours and 24 hours dealy scans. Scintigrams obtained after a 24 hours delay produced the best imaging results. All viable tumors and metastatic lesions were well delineated in the scintigrams. Blood pool radioactivity was minimal as evident by non-visualization of the heart and confirmed by tissue disbutrition data.

Post-mortem findings confirmed the locations of these neoplasms that corresponded to areas of increased radioactivity found in the scans. On histologic grounds, these tumors were found to be malignant mammary adenocarcinoma. Optimum scans were obtained 18-24 hours post injection of the radiopharmaceutical. Tissue distribution studies demonstrated high uptake of $^{99m}$Tc-HPD in neoplastic tissues as compared to blood and various organs of normal Swiss white mice (See Table I).

The following examples illustrate the labeling procedure for preparing $^{99m}$Tc-Hematoporphyrin derivative($^{99m}$Tc-HPD):

EXAMPLE I

Procedure for labeling hematoporphyrin derivative with $^{99m}$Tc

1. Inject up to 2 ml(60-200 mCi) of $^{99m}$Tc-pertechnetate normal saline solution into a sterile evacuated serum vial containing 0.5 ml of a solution of 0.1 mg stannous chloride in 0.05N hydrochloric acid. Mix the content of the reaction vial vigorously for 1-10 minutes to allow complete reduction of $^{99m}$Tc-pertechnetate.
2. Raise the pH of the mixture of step (1) to 7.4 by adding 0.5-1 ml 2% sodium citrate solution previously adjusted to pH 12.4 with 1N sodium hydroxide (NaOH).
3. Immediately inject 1 ml (5-10 mg) of the aqueous HPD solution into the reaction vial containing the admixture from step (2) slowly with gentle swirling.
4. Incubate the contents of the reaction vial at room temperature for 10-30 min. HPD is firmly labeled and ready for use without additional purification steps.
5. Perform complete qualitative and quantitative radiochemical analyses. The final concentration should be in the range of 15-50 mCi $^{99m}$Tc-HPD/ml.
6. For scintigraphic imaging, a dose of 3-25 mCi $^{99m}$Tc-HPD is sufficient to detect various types of neoplasm by scanning the patient with a rectilinear scanner or an Anger scintillation camera and by observing areas of increased radioactivity at the sites of these lesions as seen in the scans.

EXAMPLE II

Formulation of the non-radioactive labeling reagent kit for preparing $^{99m}$Tc-HPD injection Essentially, the labeling reagent kit consists of three basic components each aseptically prepared and packaged separately in sterile apyrogenic ampoule or serum vials. The labeling reagent kit is to be stored at room temperature or at 2°-8° C. When properly prepared, lyophilized and stored under nitrogen, it is stable for more than 2 years.

Vial 1. Stannous reducing reagent. Each vial contains 0.1-5 mg of stannous chloride dissolved in 0.05N to 0.1N HCl solution. The content of the vial is lyophilized and stored under nitrogen.

Vial 2. Citrate complexing reagent. Each vial contains 1-2 ml of an aqueous solution of 2% sodium citrate made alkaline to pH 12.4 with 1N NaOH solution. The content of the vial is lyophilized and stored under nitrogen. This reagent is to be recon-

TABLE I

Ratio of tumor to blood and various organs of normal Swiss white mice (n = 3) based on percent injected dose per gram tissue. The animals were sacrificed 24 hours post I.P. injection of 5 mCi $^{99m}$Tc-HPD.

| Case No. | RATIO OF TUMOR TO | | | | | | |
| --- | --- | --- | --- | --- | --- | --- | --- |
| | Blood | Heart | Lung | Liver | Spleen | Stomach | Kidney |
| 1. Metastatic lung CA | 60 | 39 | 18 | 8 | 4 | 4 | 4 |
| 2. Metastatic liver CA | 41 | 27 | 12 | 5 | 3 | 3 | 2 |
| 3. Mammary adenocarcinoma | 28 | 18 | 8 | 4 | 2 | 2 | 2 |
| 4. Mammary adenocarcinoma | 24 | 15 | 7 | 3 | 2 | 1 | 2 |
| 5. Metastatic liver CA | 27 | 17 | 8 | 3 | 2 | 2 | 2 |
| 6. Metastatic kidney CA | 40 | 26 | 12 | 5 | 3 | 3 | 3 | stituted with 1-2 ml Water for Injection, U.S.P. at time of use.

Vial 3. Hematoporphyrin derivative solution. Each dark amber-colored ampoule or serum vial contains 5-10 mg of HPD dissolved in 1 ml pH 7.4 normal saline This reagent should not be lyophilized but stored in liquid form at room temperature or at 2°-8° C.

EXAMPLE III

Procedure of preparing $^{99m}$Tc-HPD injection utilizing the labeling reagent kit.

The directions outlined below must be carefully followed for optimum preparation of $^{99m}$Tc-HPD injection:
1. Remove the kit from the refrigerator and warm to room temperature before continuing.
2. Reconstitute the citrate complexing reagent of Vial No. 2 with 1-2 ml of Water for Injection, U.S.P. until completely dissolved.
3. Aseptically inject 2 ml sterile $^{99m}$Tc-pertechnetate normal saline solution providing up to 200 mCi of radioactivity into the reaction vial containing the stannous reducing reagent (Vial No. 1) and withdraw an equal volume of air.
4. Shake the contents of the reaction vial vigorously for 1 minute and incubate at room temperature for additional 5-10 minutes to allow complete reduction of $^{99m}$Tc.
5. Aseptically inject 0.5-1 ml of the reconstituted pH 12.4 sodium citrate/NaOH solution of Vial No. 2 into the reaction vial (Vial No. 1) to bring the pH of the admixture to 7.4.
6. Inject 1 ml of the HPD solution into the reaction vial slowly with gentle swirling.
7. Incubate the contents of the reaction vial at room temperature for 10-30 minutes after mixing to allow maximum labeling.
8. Do not use the preparation after 8 hours from time of formulation.

The above examples and the described procedures are for illustrative purposes only and are not intended to be limiting of the scope of the invention. It will be apparent to those skilled in the art that both may be modified within the scope of the invention defined in the following claims.

I claim:
1. A method of labeling porphyrin compounds, related analogs, derivatives and substances containing porphyrin with the radionuclides of Technetium(Tc) at physiologic pH 7-8 condition which comprises the sequential steps of:
   a. treating the radionuclide of technetium with a reducing agent at room temperature for 1-10 minutes;
   b. raising the pH of the acidic mixture of step (a) to 7.4 with a sufficient amount of alkaline citrate complexing reagent;
   c. binding of the radionuclide of technetium to the porphyrin ligand by adding 1-10 ml of an aqueous solution of the porphyrin compound desired to be labeled to the admixture of step (b) and incubating the admixture at room temperature for 30 minutes.
2. A method according to claim 1, wherein said radionuclides of technetium is selected from the group consisting $^{99m}$Tc, $^{95m}$Tc and $^{99}$Tc.
3. A method according to claim 2, wherein said radionuclide of technetium is an aqueous solution of sodium pertechnetate in normal saline providing from 1 mCi to 5000 mCi of radioactivity.
4. A method according to claim 1, wherein said reducing agent is stannous ions selected from the group consisting stannous chloride, stannous fluoride or stannous tartrate.
5. A method according to claim 4, wherein said stannous reducing agent is present in the amount of 0.1-10 mg dissolved in 0.05-0.1N hydrochloric acid(HCl).
6. A method according to claim 5, wherein said stannous reducing agent is present in the amount of 0.2-5 mg per ml of 0.05N HCl.
7. A method according to claim 1, wherein said alkaline citrate complexing reagent is an aqueous solution of 0.5-10% sodium citrate made alkaline to pH above 8 with 1N NaOH solution.
8. A method according to claim 7, wherein said alkaline citrate complexing reagent is an aqueous solution of 2% sodium citrate having a pH of 12.4.
9. A method according to claim 1, wherein said porphyrin compound is selected from the group consisting coproporphyrins, protoporphyrins, uroporphyrins, hematoporphyrin and hematoporphyrin derivative(HPD).
10. A method according to claim 9, wherein said porphyrin compound is dissolved in an aqueous medium having a pH of above 7.
11. A method according to claim 10, wherein said porphyrin compound is present in the amount of 0.1-1000 mg dissolved in distilled water or normal saline adjusted to a pH of 7-8 with 0.1 to 1N NaOH.
12. A method according to claim 11, wherein said porphyrin compound is present in the amount of 5-100 mg dissolved in pH 7.4 normal saline together with any pharmaceutically acceptable preservative or stabilizer.
13. A method of labeling hematoporphyrin derivative(HPD) with $^{99m}$Tc at physiologic pH 7-8 condition producing a diagnostic composition suitable for radiologic imaging of neoplasms in man or in animal comprising the sequential steps of:
   a. treating 2-3 ml(60-200 mCi) of $^{99m}$Tc-pertechnetate in normal saline with 0.5 ml of a solution of 0.1-5 mg stannous chloride, stannous fluoride or stannous tartrate in 0.05N HCl solution at room temperature for 10 minutes;
   b. raising the pH of the acidic mixture of step (a) to 7.4 with a sufficient amount of the pH 12.4 sodium citrate/NaOH solution;
   c. adding 0.5-1 ml(5-10 mg) HPD solution to the neutralized mixture of step (b) and incubating the admixture at room temperature for 10-30 minutes.
14. Hematoporphyrin derivative(HPD) a compound selected from the group of porphyrins is labeled with $^{99m}$Tc according to the method of claim 13.
15. A method of localizing and detecting neoplasms in man or in animal by scintigraphic imaging procedures comprising;
   a. administering intravenously to said mammal 0.1-50 mCi of $^{99m}$Tc-HPD labeled according to the method of claim 13;
   b. scanning said mammal with a conventional scintillation Anger camera or a rectilinear scanner at various times intervals from 0.5-24 hours;
   c. observing increasing radioactivity accumulated at the sites of these tumors as seen in the scintigrams.
16. A kit for labeling porphyrin compounds, related analogs, derivatives and substances containing porphy- rin with the radionuclides of technetium at physiologic pH 7-8 condition comprising a stannous reducing agent, an alkaline citrate complexing reagent and an aqueous solution of a porphyrin compound desired to be labeled with the radionuclide aseptically prepared and packaged separately in sealed, sterile, apyrogenic containers wherein said kit is used with a solution of $^{99m}$Tc-, $^{95m}$Tc- or $^{99}$Tc-pertechnetate in normal saline.

17. A kit according to claim 16, wherein said stannous reducing agent is stannous ions selected from the group consisting stannous chloride, stannous fluoride or stannous tartrate.

18. A kit according to claim 17, wherein stannous reducing agent is dissolved in 0.05-0.1N HCl solution in a concentration of 0.1-5 mg/ml.

19. A kit according to claim 18, wherein said stannous reducing agent is present in the amount of 0.2-5 mg per ml of 0.05N HCl solution and is packaged in the form of a freeze-dried solid.

20. A kit according to claim 16, wherein said alkaline citrate complexing reagent is an aqueous solution of 0.5-10% sodium citrate made alkaline to a pH above 8 with 1N NaOH.

21. A kit according to claim 20, wherein 1-5 ml of an aqueous solution of 2% sodium citrate at pH 12.4 is packaged in the form of a freeze-dried solid as said alkaline citrate complexing reagent.

22. A kit according to claim 16, wherein said porphyrin compound is selected from the group consisting coproporphyrins, protoporphyrins, uroporphyrins, hematoporphyrin and hematoporphyrin derivative(HPD).

23. A kit according to claim 22, wherein said porphyrin compound is HPD dissolved in an aqueous medium in the concentration of 1-100 mg/ml having a pH of 7-8.

24. A kit according to claim 23, wherein said HPD is present in the amount of 5-10 mg dissolved in 1-2 ml pH 7.4 normal saline together with any pharmaceutically acceptable preservative or stabilizer.

25. A method of preparing $^{99m}$Tc-labeled HPD injection at physiologic pH 7-8 condition using the sterile labeling reagent kit of claim 16 with a solution of $^{99m}$Tc-pertechnetate in normal saline producing a pharmaceutical composition suitable for radiologic imaging of neoplasms in man or in animal which comprises the sequential steps of:
  a. reconstituting the alkaline citrate complexing reagent with 1-5 ml of Water for Injection until completely dissolved;
  b. treating the freeze-dried stannous reducing agent with 2-3 ml (60-200 mCi) $^{99m}$Tc-pertechnetate in normal saline for about 1-10 minutes;
  c. raising the pH of the mixture of step (b) to 7.4 with 0.5-1 ml of the reconstituted alkaline citrate complexing reagent;
  d. adding to the neutralized admixture of step (c) 1 ml of the HPD solution and incubating the admixture at room temperature for 10-30 minutes.

* * * * *